(12) United States Patent
Frankard et al.

(10) Patent No.: US 8,227,664 B2
(45) Date of Patent: Jul. 24, 2012

(54) PLANTS HAVING INCREASED YIELD AND METHOD FOR MAKING THE SAME

(75) Inventors: Valerie Frankard, Sint-Genesius-Rode (BE); Vladmir Mironov, Ghent (BE)

(73) Assignee: CropDesign N.V., Gent (BE)

( * ) Notice: Subject to any disclaimer, the term of this patent is extended or adjusted under 35 U.S.C. 154(b) by 1000 days.

(21) Appl. No.: 10/584,024

(22) PCT Filed: Dec. 22, 2004

(86) PCT No.: PCT/EP2004/053683
§ 371 (c)(1),
(2), (4) Date: Apr. 30, 2008

(87) PCT Pub. No.: WO2005/061702
PCT Pub. Date: Jul. 7, 2005

(65) Prior Publication Data
US 2008/0229445 A1    Sep. 18, 2008

Related U.S. Application Data

(60) Provisional application No. 60/532,287, filed on Dec. 22, 2003.

(51) Int. Cl.
*C12N 15/82* (2006.01)
*A01H 5/00* (2006.01)

(52) U.S. Cl. ......... 800/290; 800/287; 800/289; 800/298

(58) Field of Classification Search .................. None
See application file for complete search history.

(56) References Cited

FOREIGN PATENT DOCUMENTS

| WO | WO 98/03631 |   | 1/1998  |
|----|-------------|---|---------|
| WO | WO 00/65040 | * | 11/2000 |
| WO | WO 01/85946 | * | 11/2001 |
| WO | WO 01/85946 A2 | | 11/2001 |

OTHER PUBLICATIONS

Roudier F. et al. The Medicago species A2-type cyclin is auxin regulated and involved in meristem formation but dispensable for endoreduplication-associated developmental programs. Plant Physiol. Mar. 2003;131(3):1091-103.*
GenBank Accession No. AAK81695, Sep. 1, 2001, cyclin A2 [*Medicago sativa*].*
Renaudin JP et al. Plant cyclins: a unified nomenclature for plant A-, B- and D-type cyclins based on sequence organization. Plant Mol Biol. Dec. 1996;32(6):1003-18. Review.*
Setiady YY et al. Tobacco mitotic cyclins: cloning, characterization, gene expression and functional assay. Plant J. Dec. 1995;8(6):949-57.*
Chaubet-Gigot N. Plant A-type cyclins. Plant Mol Biol. Aug. 2000;43(5-6):659-75. Review.*
Chaubet-Gigot, N. (2000), "Plant A-Type Cyclins" *Plant Molecular Biology* 43:659-675.
Cockcroft, C. et al. (2000), "Cyclin D Control of Growth Rate in Plants" *Nature* 405: 575-579.
Roudier, F. et al. (2003), The Medicago Species A2-Type Cyclin is Auxin Regulated and Involved in Meristem Formation But Dispensable for Endoreduplication-Associated Developmental Programs. *Plant Physiology* 131:1091-1103.
Wyrzykowska, J. et al. (2002), "Manipulation of Leaf Shape by Modulation of Cell Division", *Development* 129: 957-964.
Yu, Y. et al. (2003), "The Tobacco A-Type Cyclin, Nicta;CYCA3;2, at the Nexux of Cell Division and Differentiation", *Plant Cell* 15: 2763-2777.

* cited by examiner

*Primary Examiner* — Cynthia Collins
(74) *Attorney, Agent, or Firm* — Ann R. Pokalsky, Esq.; Dilworth & Barrese, LLP

(57) ABSTRACT

The invention concerns a method for increasing plant yield by introducing into a plant a cyclin A nucleic acid, preferably encoding a cyclin A protein, which cyclin A nucleic acid is operably linked to a seed-preferred promoter. By using this method, plant yield may be increased in optimal and suboptimal growing conditions. The method results in plants having increased yield relative to corresponding wild type plants and relative to transgenic plants constitutively expressing cyclin A.

9 Claims, 5 Drawing Sheets

| Gene name | Plant accession | Motif 1 | Motif 2 |
|---|---|---|---|
| Cyclin A2;1 | Arabidopsis At5g25380 | WLVEVSEEYKLVSDT SEQ ID NO: 8 | ELTLTEYTFRLFLPS SEQ ID NO: 20 |
| Cyclin A2;2 | Arabidopsis At5g11300 | WLVEVSDDYKLVPDT SEQ ID NO: 9 | ELTLVEYSFLRFLPS SEQ ID NO: 21 |
| Cyclin A2;3 | Arabidopsis At1g15570 | WLVEVSEEYTLASDT SEQ ID NO: 10 | ELTLIDYHFLKFLPS SEQ ID NO: 22 |
| Cyclin A2;4 | Arabidopsis At5g43080 | WLVEVSEEYTLVPDT SEQ ID NO: 11 | ELTLMDYPFLKFLPS SEQ ID NO: 23 |
| Cyclin A2type | Rice AK106653 | WLVEVSEEYKLVPDT SEQ ID NO: 12 | ELTLIDYSFLKFLPS SEQ ID NO: 24 |
| Cyclin A2type | Medicago AAK81695 | WLVEVSEGYKLQANT SEQ ID NO: 13 | ELTLMNYGFLNFLPS SEQ ID NO: 25 |
| Cyclin A2 type | Nicotiana BAA09367 | WLVEVSEEYRLVPDT SEQ ID NO: 14 | ELTLVDYGFLKFLPS SEQ ID NO: 26 |
| Cyclin A1;1 | Arabidopsis At1g44110 | WLIEVSEEYRLVPET SEQ ID NO: 15 | ELSLLEYTMLSHSPS SEQ ID NO: 27 |
| Cyclin A1;2 | Arabidopsis At1g77390 | WLVEVAEEYRLSPET SEQ ID NO: 16 | ELSLLDYAMLRYAPS SEQ ID NO: 28 |
| Cyclin A3;1 | Arabidopsis at5g43080 | WLVEVAEEYKLLSDT SEQ ID NO: 17 | ELSMLDYQSVKFLPS SEQ ID NO: 29 |
| Cyclin A1.1 type | Rice BAA86628 | WLVEVAEEYRLVPDT SEQ ID NO: 18 | ELSLLEYNLLSYPPS SEQ ID NO: 30 |
| Cyclin B1;1 | Arabidopsis At4g37490 | WLIDVHVRFELNPET SEQ ID NO: 19 | ELGVMHYDTMIMFSPS SEQ ID NO: 31 |

FIGURE 3

SEQUENCE LISTING

SEQ ID NO 01: DNA sequence of Cyclin A2;2 (A variant of the coding sequence of the sequence deposited under accession number NM_121168 contains a G instead of C on position 851 (boxed) and a T instead of C on position 1295 (boxed))

atgtattgctcttcttcgatgcatccaaatgcaaacaaagaaaatatctctacttcagatgt
acaggagagttttgtacgaataacgagatcacgagctaaaaaagccatgggaagaggagtat
caatacctccaacaaaaccttcttttaaacagcaaaagagacgtgcagtacttaaggatgtg
agtaatacctctgcagatattatttattcagaacttcgaaagggaggcaacatcaaggcaaa
cagaaaatgtctaaaagagcctaaaaaagcagcaaaggaaggtgctaacagtgccatggata
ttctggtagatatgcatacagaaaaatcaaaattagcagaagatttgtccaagatcaggatg
gctgaagcccaagatgtctctctttcaaactttaaagatgaagaaattactgagcaacaaga
agatggatcaggtgtcatggagttacttcaagttgtagatattgattccaacgtcgaagatc
cacagtgttgcagcttgtatgctgctgatatatatgacaacatacatgttgcagagcttcaa
caacgacccttggctaattatatggagcttgtgcagcgagatatcgacccagacatgagaaa
gattctgattgactggcttgtagaagtttctgacgactacaagctggttccagatacgcttt
accttacagtgaatcttatcgaccggtttctgtccaacagttacattgaaaggcaaagactc
cagctccttggtgtctcttgcatgcttatagcttcaaaatatgaagagctttccgcaccagg
ggtggaggagttttgcttcattacggccaacacatacacaagacagaagtgctgagcatgg
agattcaaattctaaattttgtgcactttagattatcggttcctaccaccaaaacatttctg
aggcggttcattaaagcagctcaagcttcgtacaaggtgcctttcattgaactggagtattt
agcaaactatctcgccgaattgacactggtggaatatagtttcctaaggttcctgccatcac
taattgctgcttcagctgttttcctagcccgatggacactcgaccaaactgaccatccttgg
aaccctactctgcaacactacaccagatatgaggtagctgagctgaagaacacagttctcgc
catggaggacttgcagctcaacaccagtggctgtactctcgctgccacccgtgagaaataca
accaaccaaagtttaagagcgtggcaaagctgacatctcccaaacgagtcacatcactattc
tcaagatga

SEQ ID NO 02: protein sequence of Cyclin A2;2 (A variant of the sequence deposited under accession number NP_568248 contains an arginine instead of a proline on position 284 (boxed) and a phenylalanine instead of a serine on position 432 (boxed))

MYCSSSMHPNANKENISTSDVQESFVRITRSRAKKAMGRGVSIPPTKPSFKQQKRRAVLKDV
SNTSADIIYSELRKGGNIKANRKCLKEPKKAAKEGANSAMDILVDMHTEKSKLAEDLSKIRM
AEAQDVSLSNFKDEEITEQQEDGSGVMELLQVVDIDSNVEDPQCCSLYAADIYDNIHVAELQ
QRPLANYMELVQRDIDPDMRKILIDWLVEVSDDYKLVPDTLYLTVNLIDRFLSNSYIERQRL
QLLGVSCMLIASKYEELSAPGVEEFCFITANTYTRPEVLSMEIQILNFVHFRLSVPTTKTFL
RRFIKAAQASYKVPFIELEYLANYLAELTLVEYSFLRFLPSLIAASAVFLARWTLDQTDHPW
NPTLQHYTRYEVAELKNTVLAMEDLQLNTSGCTLAATREKYNQPKFKSVAKLTSPKRVTSLF
SR

FIGURE 4

SEQ ID NO 03: DNA sequence of the prolamin promoter cttctacatcggcttaggtgtagcaacacgactttattattattattattattattatt
attttacaaaaatataaaatagatcagtccctcaccacaagtagagcaagttggtgagttat
tgtaaagttctacaaagctaatttaaaagttattgcattaacttatttcatattacaaacaa
gagtgtcaatggaacaatgaaaaccatatgacatactataattttgttttattattgaaat
tatataattcaaagagaataaatccacatagccgtaaagttctacatgtggtgcattaccaa
aatatatatagcttacaaaacatgacaagcttagtttgaaaaattgcaatccttatcacatt
gacacataaagtgagtgatgagtcataatattattttctttgctacccatcatgtatatatg
atagccacaaagttactttgatgatgatatcaaagaacatttttaggtgcacctaacagaat
atccaaataatatgactcacttagatcataatagagcatcaagtaaaactaacactctaaag
caaccgatgggaaagcatctataaatagacaagcacaatgaaaatcctcatcatccttcacc
acaattcaaatattatagttgaagcatagtagta

SEQ ID NO 04: primer sequence (primer PRM582)

ggggacaagtttgtacaaaaaagcaggcttcacaatgtattgctcttcttcgatgc

SEQ ID NO 05: primer sequence (primer PRM583)

ggggaccactttgtacaagaaagctgggtgcttggtgtcatcttgagaatag

FIGURE 4 (continued)

PLANTS HAVING INCREASED YIELD AND METHOD FOR MAKING THE SAME

This application is a section 371 application of PCT/EP2004/053683, filed Dec. 22, 2004, which claims the benefit under 35 U.S.C. §119(e) of U.S. Provisional Application 60/532,287, filed Dec. 22, 2003.

The present invention relates generally to the field of molecular biology and concerns a method for increasing plant yield. More specifically, the present invention concerns a method for increasing plant yield by introducing into a plant a cyclin A nucleic acid, preferably encoding a cyclin A protein, which nucleic acid is operably linked to a seed-preferred promoter. The present invention also concerns plants having increased expression of a cyclin A nucleic acid in plant seed tissue and/or modulated activity and/or levels of a cyclin A protein in plant seed tissue, which plants have increased yield relative to corresponding wild type plants and relative to corresponding transgenic plants in which cyclin A is constitutively expressed.

The ever-increasing world population and the dwindling supply of arable land available for agriculture fuel agricultural research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance are also important factors in determining yield. Crop yield may be increased by optimising one of the abovementioned factors, which may be done by modifying the inherent growth mechanisms of a plant.

The inherent growth mechanisms of a plant reside in a highly ordered sequence of events collectively known as the 'cell cycle'. Progression through the cell cycle is fundamental to the growth and development of all multi-cellular organisms and is crucial to cell proliferation. The major components of the cell cycle are highly conserved in yeast, mammals, and plants. The cell cycle is typically divided into the following sequential phases: G0-G1-S-G2-M. DNA replication or synthesis generally takes place during the S phase ("S" is for DNA synthesis) and mitotic segregation of the chromosomes occurs during the M phase (the "M" is for mitosis), with intervening gap phases, G1 (during which cells grow before DNA replication) and G2 (a period after DNA replication during which the cell prepares for division). Cell division is completed after cytokinesis, the last step of the M phase. Cells that have exited the cell cycle and that have become quiescent are said to be in the G0 phase. Cells in this phase can be stimulated to renter the cell cycle at the G1 phase. The "G" in G1, G2 and G0 stands for "gap". Completion of the cell cycle process allows each daughter cell during cell division to receive a full copy of the parental genome.

Cell division is controlled by two principal cell cycle events, namely initiation of DNA synthesis and initiation of mitosis. Each transition to each of these key events is controlled by a checkpoint represented by specific protein complexes (involved in DNA replication and division). The expression of genes necessary for DNA synthesis at the G1/S boundary is regulated by the E2F family of transcription factors in mammals and plant cells (La Thangue, 1994; Muller et al., 2001; De Veylder et al., 2002). Entry into the cell cycle is regulated/triggered by an E2F/Rb complex that integrates signals and allows activation of transcription of cell cycle genes. The transition between the different phases of the cell cycle, and therefore progression through the cell cycle, is driven by the formation and activation of different heterodimeric serine/threonine protein kinases, generally referred to as cyclin-dependent kinases (CDKs). A prerequisite for activity of these kinases is the physical association with a specific cyclin, the timing of activation being largely dependent upon cyclin expression. Cyclin binding induces conformational changes in the N-terminal lobe of the associating CDK and contributes to the localisation and substrate specificity of the complex. Monomeric CDKs are activated when they are associated with cyclins and thus have kinase activity. Cyclin protein levels fluctuate in the cell cycle and therefore represent a major factor in determining timing of CDK activation. The periodic activation of these complexes containing cyclins and CDK during cell cycle mediates the temporal regulation of cell-cycle transitions (checkpoints). Other factors regulating CDK activity include CDK inhibitors (CKIs or ICKs, KIPs, CIPs, INKs), CDK activating kinases (CAKs), a CDK phosphatase (Cdc25) and a CDK subunit (CKS) (Mironov et al. 1999; Reed 1996).

Three different subclasses of *Arabidopsis* A-type cyclins (A1, A2, and A3) (comprising 10 cyclins) have been described. Two A1-type genes (CYCA1;1 and CYCA1;2), four A2-type genes (CYCA2;1, CYCA2;2, CYCA2;3, and CYCA2;4), and four A3-type genes (CYCA3;1, CYCA3;2, CYCA3;3, and CYCA3;4) have been reported in Vandepoele et al. (The Plant Cell, Vol. 14, 903-916, April 2002).

International application WO 01/85946 describes several cell cycle proteins, including cyclin As. It is mentioned that the cell cycle proteins may be used in agriculture to improve the growth characteristics of a plant, such as the growth rate or size of specific tissues or organs, architecture or morphology of a plant, increased crop yield, improved tolerance to environmental stress conditions (such as drought, salt, temperature, or nutrient deprivation), improved tolerance to plant pathogens that abuse the cell cycle or as targets to facilitate the identification of inhibitors or activators of CCPs that may be useful as herbicides or plant growth regulators.

Yield may be increased in many ways, some surprising. For example, the major factor that contributed to yield enhancement of wheat and rice in the 1960s (the so-called green revolution) is the reduction in plant height (Sakamoto and Matsuoka, Current Opinion in Biotechnology 2004, 15:144-147). Having used large amounts of nitrogen fertilizer, the traditional varieties of that time grew excessively tall and toppled, leading to significant yield losses. In contrast, due to their short stature, the semi-dwarf varieties of the green revolution were lodging resistant, which resulted in a doubling of the crop yield.

It has now surprisingly been found that plant yield may be increased by introducing into a plant a cyclin A nucleic acid, preferably encoding a cyclin A protein, which cyclin A nucleic acid is operably linked to a seed-preferred promoter. Expression of a cyclin A nucleic acid under the control of a seed-preferred promoter results in a greater yield than that obtained upon expression of a cyclin A that is constitutively expressed in a plant.

Therefore according to one embodiment of the present invention there is provided a method for increasing plant yield, comprising introducing into a plant a cyclin A nucleic acid, preferably encoding a cyclin A protein, which cyclin A nucleic acid is operably linked to a seed-preferred promoter.

Performance of the method according to the present invention results in increased plant yield. The term "increased yield" as defined herein encompasses an increase in biomass (weight) in one or more parts of a plant relative to the biomass of control plants. The term also encompasses an increase in seed yield, which includes an increase in the biomass of the seed (seed weight) and/or an increase in the number of (filled) seeds and/or an increase in the size of the seeds and/or an increase in seed volume, each relative to control plants. An increase in seed size and/or volume may also influence the composition of seeds. An increase in seed yield may result from an increase in the number and/or size of flowers. An increase in yield may also increase the harvest index, which is expressed as a ratio of the total biomass over the yield of harvestable parts, such as seeds. An increase in yield may also increase the thousand kernel weight (TKW), which is extrapolated from the number of filled seeds counted and their total weight.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, among others. Taking rice as an example, a yield increase may be manifested by an increase in one or more of the following: number of plants per hectare or acre, number of panicles per plant, number of spikelets per panicle, the number of flowers per panicle, an increase in the seed filling rate, an increase in thousand kernel weight, among others.

Yield may be further increased, or yield may be further evaluated, in hybrid plants. A crop such as corn is typically commercialised as a hybrid. The aim of field crop breeding is to combine various desirable traits in a single variety or in a hybrid. Breeding occurs through different techniques that take advantage of the plant's pollination method (self pollination, as is the case with rice or cross pollination, as is the case with corn). Breeding of cereals often involves self-pollination and cross-pollination steps. Taking corn as an example, the production of new varieties frequently entails the development, selection and production of inbred parental lines which are subsequently used to produce hybrid corn with certain desired characteristics. Hence, the development of corn hybrids requires the development of homozygous inbred lines, the crossing of these lines and the evaluation of these crosses (hybrid). The introduction of desirable characteristics may then be made by crossing (genetic introduction) or by molecular introduction through transformation techniques. To determine the field performance of the product, evaluation of the new crop can be made on a homogenous population of homozygous inbred plants, or on a hybrid between two homozygous inbred lines. The aforementioned techniques are well known in the art.

More particularly, the increased yield is manifested as one or more of the following: increased seed weight, increased number of filled seeds, increased seed number, increased seed size, increased harvest index, increased thousand kernel weight and modified seed composition, each relative to control plants. Therefore, according to the present invention, there is provided a method for increasing plant yield, wherein the increased plant yield is selected from one or more of: increased seed weight, increased number of filled seeds, increased seed number, increased seed size, increased harvest index, increased thousand kernel weight and modified seed composition, each relative to control plants, which method comprises introducing into a plant a cyclin A nucleic acid, preferably encoding a cyclin A protein, which cyclin A nucleic acid is operably linked to a seed-preferred promoter.

Since the transgenic plants according to the present invention have increased yield, it is likely that these plants exhibit an increased growth rate (during at least part of their life cycle) relative to the growth rate of control plants at a corresponding stage in their life cycle. The increased growth rate may be specific to one or more parts of a plant (including seeds), or may be throughout substantially the whole plant. In the case of seeds, especially those of cereals, seed maturity may be linked to moisture content of the seeds when intact on a plant. The moisture content, which gives an indication of the maturity of the seed, will also therefore give one indication of growth rate of the seeds compared to control plants. A person skilled in the art will be well aware, for any given plant species, of the moisture content indicative of a seed ready for harvest. Moisture content may be measured using known techniques.

Furthermore, the increase in growth rate may take place at one or more stages in the life cycle of a plant or during substantially the whole plant life cycle. Increased growth rate during the early stages in the life cycle of a plant may reflect enhanced vigour.

The increase in growth rate may alter the harvest cycle of a plant allowing plants to be sown later and/or harvested sooner than would otherwise be possible. The term "harvest cycle" as defined herein is taken to mean the time between sowing and harvesting of a plant. If the growth rate is sufficiently increased, it may allow for the sowing of further seeds of the same plant species (for example sowing and harvesting of rice plants followed by sowing and harvesting of further rice plants all within one conventional growing period). Similarly, if the growth rate is sufficiently increased, it may give rise to the possibility of sowing further seeds of different plants species (for example the sowing and harvesting of rice plants followed by, for example, the sowing and optional harvesting of soy bean, potatoes or any other suitable plant). Harvesting from the same rootstock may, in the case of some plants, take place at additional times of the year. The possibility to alter the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened.

Growth rate may be determined by deriving various parameters from growth curves plotting growth experiments, such parameters may be: T-Mid (the time taken for plants to reach 50% of their maximal size) and T-90 (time taken for plants to reach 90% of their maximal size), amongst others.

According to the present invention, performance of the methods of the invention result in plants having modified growth rate. Therefore, according to the present invention, there is provided a method for increasing the growth rate of plants, which method comprises introducing into a plant a cyclin A nucleic acid, preferably encoding a cyclin A protein, which cyclin A nucleic acid is operably linked to a seed-preferred promoter.

An increase in yield and/or growth rate also encompasses a better performance of the plant under non-stress conditions as well as under stress conditions compared to control plants. Plants typically respond to exposure to stress by growing more slowly. In conditions of severe stress, the plant may stop growing altogether. Mild stress on the other hand is defined herein as being any stress in which the plant does not stop growing altogether. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Abiotic stresses may also be caused by chemicals. Biotic stresses as typically those stresses caused by pathogens, such as bacteria, viruses, fungi and insects.

In one embodiment of the present invention, the cyclin A to be introduced into a plant is an A2-type cyclin, preferably a cyclin A2;2.

A "cyclin A nucleic acid" as defined herein is taken to mean a nucleic acid encoding a protein which in its native form comprises motif 1, which is represented as: W L V/I E V S/A D/E D/E Y K/R/T L (SEQ ID NO: 6) (motif 1), where a backslash (/) means 'or', i.e. where 'V/I' means V or I. The presence of motif 1 in an amino acid sequence allows the sequence to be identified as a cyclin A rather than any other type of cyclin.

The term "cyclin A2 nucleic acid" as defined herein is any nucleic acid encoding a protein which in its native form comprises motif 1 as identified above and additionally motif 2, which is represented as: E L T L V/I/T/M D/E/M Y T/S/H/P/G F R/L L/R/K/N F L P S (SEQ ID NO: 7) (motif 2), wherein the presence of at least two of the residues identified (- -T- - - - -F- -F- - -) (and underlined above) allow the sequence to be identified as a cyclin A2-type rather than as any other cyclin A. The dashes (-) above represent amino acid residues, where one dash is equal to one amino acid residue in a corresponding position in motif 2.

The term "cyclin A2;2 nucleic acid" as defined herein is any cyclin A nucleic acid encoding a protein having in increasing order of preference at least 65%, 70%, 75%, 80%, 85%, 90% or 95% sequence identity or similarity to the amino acid sequence represented by SEQ ID NO: 2.

A "cyclin A amino acid" or "cyclin A protein" as defined herein is taken to mean an amino acid which in its native form comprises motif 1, which is represented as: W L V/I E V S/A D/E D/E Y K/R/T L (motif 1), where a backslash (/) means 'or', i.e. where 'V/I' means V or I. The presence of motif 1 in an amino acid sequence allows the sequence to be identified as a cyclin A rather than as any other type of cyclin.

The term "cyclin A2 amino acid" or "cyclin A2 protein" as defined herein is any amino acid which in its native form comprises motif 1 as identified above and additionally motif 2, which is represented as: E L T L V/I/T/M D/E/M Y T/S/H/P/G F R/L L/R/K/N F L P S (SEQ ID NO:7) (motif 2), wherein the presence of at least two of the residues identified (- -T- - - - -F- -F- - -) (and underlined above) allow the sequence to be identified as a cyclin A2-type rather than as any other cyclin A. The dashes (-) above represent amino acid residues, where one dash is equal to one amino acid residue in a corresponding position in motif 2.

The term "cyclin A2;2 amino acid" or cyclin A2;2 protein" as defined herein is taken to mean a cyclin A protein having in increasing order of preference at least 65%, 70%, 75%, 80%, 85%, 90% or 95% homology to the amino acid sequence represented as SEQ ID NO: 2.

The cyclin A nucleic acid to be introduced into a plant may be derived from any source provided that the nucleic acid, when overexpressed in plant seed tissue, leads to increased plant yield. The nucleic acid to be introduced into a plant may be isolated from a microbial source, such as bacteria, yeast or fungi, or from a plant, algae or animal source. This nucleic acid may be substantially modified from its native form in composition and/or genomic environment through deliberate human manipulation. The nucleic acid sequence is preferably a homologous nucleic acid sequence, i.e. a nucleic acid sequence obtained from a plant, whether from the same plant species or different. The nucleic acid sequence may be isolated from a monocotyledonous or dicotyledonous species, preferably from the family Brassicaceae, further preferably from *Arabidopsis thaliana*. Most preferably the cyclin A is of the cyclin A2 type, such as a cyclin A2;1, A2;2, A2;3 or A2;4. In a particularly preferred embodiment, the cyclin A2;2 is as represented by SEQ ID NO: 1 and SEQ ID NO: 2.

Although the present invention has been exemplified with a nucleic acid represented by SEQ ID NO: 1 and an amino acid represented by SEQ ID NO: 2, the methods may also be performed using variant cyclin A amino acids and variant cyclin A nucleic acids.

Variant nucleic acid and amino acid sequences useful in practising the methods according to the invention, include:
(i) Functional portions of a cyclin A nucleic acid;
(ii) Sequences capable of hybridising to a cyclin A nucleic acid/gene;
(iii) Alternative splice variants of a cyclin A nucleic acid/gene;
(iv) Allelic variants of a cyclin A nucleic acid/gene;
(v) Variants due to the degeneracy of the genetic code; and
(vi) Homologues, derivatives and active fragments of a cyclin A protein.

The term "nucleic acid" as used herein encompasses complementary strands and the corresponding RNA, DNA, cDNA and genomic DNA. The nucleic acid may be double or single stranded.

It would be apparent to a person skilled in the art that a full length cyclin A DNA sequence is not a prerequisite to carrying out the methods according to the invention, but that functional portions of a cyclin A nucleic acid may also be employed. A functional portion refers to a piece of DNA derived or prepared from an original (larger) DNA molecule, which DNA portion, when introduced and expressed in a plant, gives plants having increased yield. The portion may comprise many genes, with or without additional control elements, or may contain just spacer sequences. Portions suitable for use in the methods according to the invention may readily be determined using routine techniques. For example, one or more deletions and/or truncations may be made to the nucleic acid sequence of SEQ ID NO: 1 without affecting its ability to perform in the methods according to the invention. Portions suitable for use in the methods according to the invention may readily be determined using routine techniques, such as by assaying for cyclin A activity and/or by following the methods described in the Examples section by simply substituting the sequence used in the actual example with the portion to be tested for functionality. A preferred portion for use in the methods of the invention is capable of encoding a protein comprising motif 1 and preferably additionally motif 2. Further preferably, the portion is a portion of a cyclin A nucleic acid as represented by SEQ ID NO: 1.

Therefore, according to another embodiment of the present invention, there is provided, a method for increasing plant yield, comprising introducing into a plant a functional portion of a cyclin A nucleic acid, preferably as represented by SEQ ID NO: 1, which functional portion is operably linked to a seed-preferred promoter.

Sequences capable of hybridising to a cyclin A nucleic acid, such as the one represented by SEQ ID NO: 1, may also be useful in performing the methods according to the invention. The term "hybridisation" as defined herein is a process wherein substantially homologous complementary nucleotide sequences anneal to each other. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to e.g. a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. High stringency conditions for hybridisation include high temperature and/or low salt concentration (salts include NaCl and $Na_3$-citrate) and/or the inclusion of formamide in the hybridisation buffer and/or lowering the concentration of compounds such as SDS (detergent) in the hybridisation buffer and/or exclusion of compounds such as dextran sulphate or polyethylene glycol (promoting molecular crowding) from the hybridisation buffer. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid sequence. Low stringency hybridisation conditions are particularly preferred to isolate nucleic acids heterologous to the DNA sequences of the invention defined supra. An example of low stringency conditions is 4-6×SSC/0.1-0.5% w/v SDS at 37-45° C. for 2-3 hours. Depending on the source and concentration of the nucleic acid involved in the hybridisation, alternative conditions of stringency may be employed, such as medium stringent conditions. Examples of medium stringent conditions include 1-4×SSC/0.25% w/v SDS at >45° C. for 2-3 hours. An example of high stringency conditions includes 0.1-1×SSC 10.1% w/v SDS at 60° C. for 1-3 hours. The skilled man will be aware of various parameters which may be altered during hybridisation and washing and which will either maintain or change the stringency conditions. Elements contributing to heterology include allelism, degeneration of the genetic code and differences in preferred codon usage.

Preferred sequences capable of hybridising to a cyclin A nucleic acid, such as the one represented as SEQ ID NO: 1, are those hybridising sequences capable of encoding a protein comprising motif 1 and preferably additionally motif 2. Hybridising sequences suitable for use in the methods according to the invention may readily be determined using routine techniques, such as by assaying for cyclin A activity and/or by following the methods described in the Examples section by simply substituting the sequence used in the actual example with the hybridising sequence to be tested for functionality.

Therefore, according to another embodiment of the present invention, there is provided, a method for increasing plant yield, comprising introducing into a plant a nucleic acid capable of hybridising to a cyclin A nucleic acid as defined hereinabove, preferably to a cyclin A nucleic acid as represented by SEQ ID NO: 1, which hybridising sequence is operably linked to a seed-preferred promoter.

The methods according to the present invention may also be practised using an alternative splice variant of a cyclin A nucleic acid, such as the one represented by SEQ ID NO: 1. The term "alternative splice variant" as used herein encompasses variants of a nucleic acid sequence in which selected introns and/or exons have been excised, replaced or added. Such variants will be ones in which the biological activity of the protein remains unaffected, which may be achieved by selectively retaining functional segments of the protein encoded by the nucleic acid. Such splice variants may be found in nature or can be manmade. Methods for making such splice variants are well known in the art. Preferred splice variants encode a protein comprising motif 1 and preferably additionally motif 2. Splice variants of a cyclin A nucleic acid suitable for use in the methods according to the invention may readily be determined using routine techniques, such as by assaying for cyclin A activity and/or by following the methods described in the Examples section by simply substituting the sequence used in the actual example with the splice variant to be tested for functionality.

Therefore, according to another embodiment of the present invention, there is provided, a method for increasing plant yield, comprising introducing into a plant a splice variant of a cyclin A nucleic acid, preferably a splice variant of a nucleic acid sequence as represented by SEQ ID NO: 1, which splice variant is operably linked to a seed-preferred promoter.

Advantageously, the methods according to the present invention may also be practised using allelic variants of a cyclin A nucleic acid, preferably allelic variants of a cyclin A nucleic acid as represented by SEQ ID NO: 1. Allelic variants exist in nature and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp). SNPs and INDELs form the largest set of sequence variants in naturally occurring polymorphic strains of most organisms. Preferred allelic variants encode a protein comprising motif 1 and preferably additionally motif 2. Allelic variants of a cyclin A nucleic acid suitable for use in the methods according to the invention may readily be determined using routine techniques, such as by assaying for cyclin A activity and/or by following the methods described in the Examples section by simply substituting the sequence used in the actual example with the allelic variant to be tested for functionality.

Therefore, according to another aspect of the present invention, there is provided, a method for increasing plant yield, comprising introducing into a plant an allelic variant of a cyclin A nucleic acid, preferably an allelic variant of a cyclin A nucleic acid as represented by SEQ ID NO: 1, which allelic variant is operably linked to a seed-preferred promoter.

Examples of variant cyclin A amino acids include homologues, derivatives and active fragments of a cyclin A represented by SEQ ID NO: 2.

"Homologues" of a cyclin A protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company). Preferably, the homologues have in increasing order of preference at least 40%, 45%, 50%, 55%, 60%, 65%, 70%, 75%, 80%, 85%, 90%, 95%, 96%, 97%, 98% or 99% or more sequence identity (functional identity) to the cyclin A represented by SEQ ID NO: 2. Homologues having at least 40% sequence identity encompass cyclin As without covering any other cyclin class.

Two special forms of homology, orthologs and paralogs, are evolutionary concepts used to describe ancestral relationships of genes. The term "paralogous" relates to gene-duplications within the genome of a species leading to paralogous genes. The term "orthologous" relates to homologous genes in different organisms due to ancestral relationship.

Othologues in, for example, monocot plant species may easily be found by performing a so-called reciprocal blast search. This may be done by a first blast involving blasting the sequence in question (SEQ ID NO: 1 or SEQ ID NO: 2) against any sequence database, such as the publicly available NCBI database which may be found at: ncbi.nlm.nih.gov. If orthologues in rice were sought, the sequence in question would be blasted against, for example, the 28,469 full-length cDNA clones from Oryza sativa Nipponbare available at NCBI. BLASTn may be used when starting from nucleotides or TBLASTX when starting from the protein, with standard default values (expectation 10, alignment 50). The blast results may be filtered. The full-length sequences of either the filtered results or the non-filtered results are then blasted back (second blast) against the sequence in question (SEQ ID NO: 1 or 2). The results of the first and second blasts are then compared. In the case of large families, ClustalW is used followed by a neighbour joining tree to help visualize the clustering. Examples of cyclin A orthologues include the sequences deposited under the following accession numbers: a rice orthologue deposited under protein accession number AK106653 (cyclin A2 type), a rice orthologue deposited under protein accession number BAA86628 (cyclin A1 type) and a corn orthologue deposited under accession AAC50013.

The term "homologues" as used herein also encompasses paralogues and orthologues of the proteins useful in the methods according to the invention.

"Substitutional variants" of a protein are those in which at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues and deletions will range from about 1 to 20 residues. Preferably, amino acid substitutions comprise conservative amino acid substitutions.

"Insertional variants" of a protein are those in which one or more amino acid residues are introduced into a predetermined site in a protein. Insertions can comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)6-tag, glutathione S-transferase-tag, protein A, maltose-binding protein, dihydrofolate reductase, Tag-100 epitope, c-myc epitope, FLAG®-epitope, lacZ, CMP (calmodulin-binding peptide), HA epitope, protein C epitope and VSV epitope.

"Deletion variants" of a protein are characterised by the removal of one or more amino acids from the protein. Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Methods for the search and identification of cyclin A homologues would be well within the realm of a person skilled in the art. Methods for the alignment of sequences for comparison are well known in the art, such methods include GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percent sequence identity and performs a statistical analysis of the similarity between the two sequences. The software for performing BLAST analysis is publicly available through the National Centre for Biotechnology Information.

The term "derivatives" refers to peptides, oligopeptides, polypeptides, proteins and enzymes which may comprise substitutions, deletions or additions of naturally and non-naturally occurring amino acid residues compared to a cyclin A amino acid sequence, such as the one represented by SEQ ID NO: 2. "Derivatives" of a cyclin A protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence such as, for example, a reporter molecule which is bound to facilitate its detection, and non-naturally occurring amino acid residues relative to the amino acid sequence of a naturally-occurring protein.

"Active fragments" of a cyclin A protein comprise at least motif 1 and preferably additionally motif 2 and retain similar biological and/or functional activity to the naturally occurring protein.

Plants are transformed with a vector comprising the sequence of interest (i.e., the cyclin A nucleic acid), which sequence is operably linked to a seed-preferred promoter.

Therefore according to another embodiment of the present invention, there is provided a construct comprising:
(i) a cyclin A nucleic acid;
(ii) a seed-preferred promoter; and optionally
(iii) a transcription termination sequence.

The cyclin A nucleic acid may be any of the aforementioned cyclin A sequences including the cyclin A variant sequences. Suitable seed-preferred promoters are defined hereinafter.

The terms "regulatory element", "control sequence" and "promoter" are all used herein interchangeably and are to be taken in a broad context to refer to regulatory nucleic acid sequences capable of effecting expression of the sequences to which they are ligated. The term "operably linked" as used herein refers to a functional linkage between the promoter sequence and the gene of interest, such that the promoter sequence is able to initiate transcription of the gene of interest.

Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ.

Advantageously, the methods of the invention may be performed using any seed-preferred promoter. A seed-preferred promoter in the context of the present invention is a promoter that is predominantly active in seed tissue, but not necessarily exclusively active in seed-tissue. Seed tissue includes any part of the seed including the seed coat, the aleurone layer, the endosperm (for monocots and endospermic dicots), the embryo (scutellum, epiblast, plumule, radicle for monocots; cotyledons, hypocotyl, and radicle for dicots). A preferred promoter for practicing the method according to the invention is one which is active in the endosperm, such as the alpha globulin promoter from rice, the oat globulin promoter, the rice or wheat glutelin promoter, blz2, rice transcription factor RISBZ1. Particularly preferred is a promoter active in the endosperm, which promoter is preferably active during and after germination, such as the prolamin promoter from rice.

Examples of suitable promoters for practicing the methods of the present invention are provides in Table 1 below.

TABLE 1

Seed Preferred promoters

| GENE SOURCE | EXPRESSION PATTERN | REFERENCE |
| --- | --- | --- |
| seed-specific genes | seed | Simon, et al., *Plant Mol. Biol.* 5: 191, 1985; Scofield, et al., *J. Biol. Chem.* 262: 12202, 1987.; Baszczynski, et al., *Plant Mol. Biol.* 14: 633, 1990. |
| Brazil Nut albumin | seed | Pearson, et al., *Plant Mol. Biol.* 18: 235-245, 1992. |
| legumin | seed | Ellis, et al., *Plant Mol. Biol.* 10: 203-214, 1988. |
| glutelin (rice) | seed | Takaiwa, et al., *Mol. Gen. Genet.* 208: 15-22, 1986; Takaiwa, et al., *FEBS Letts.* 221: 43-47, 1987. |
| zein | seed | Matzke et al *Plant Mol Biol*, 14(3): 323-32 1990 |
| napA | seed | Stalberg, et al, *Planta* 199: 515-519, 1996. |
| wheat LMW and HMW glutenin-1 | endosperm | *Mol Gen Genet* 216:81-90, 1989; *NAR* 17: 461-2, 1989 |
| wheat SPA | seed | Albani et al, *Plant Cell*, 9: 171-184, 1997 |
| wheat α, β, γ-gliadins | endosperm | *EMBO* 3: 1409-15, 1984 |
| barley ltr1 promoter | endosperm | |
| barley B1, C, D, hordein | endosperm | *Theor Appl Gen* 98: 1253-62, 1999; *Plant J* 4: 343-55, 1993; *Mol Gen Genet* 250: 750-60, 1996 |
| barley DOF | endosperm | Mena et al, *The Plant Journal*, 116(1): 53-62, 1998 |
| blz2 | endosperm | EP99106056.7 |
| synthetic promoter | endosperm | Vicente-Carbajosa et al., *Plant J.* 13: 629-640, 1998. |
| rice prolamin NRP33 | endosperm | Wu et al, *Plant Cell Physiology* 39(8) 885-889, 1998 |
| rice α-globulin Glb-1 | endosperm | Wu et al, *Plant Cell Physiology* 39(8) 885-889, 1998 |
| rice OSH1 | embryo | Sato et al, *Proc. Natl. Acad. Sci. USA*, 93: 8117-8122, 1996 |
| rice α-globulin REB/OHP-1 | endosperm | Nakase et al. *Plant Mol. Biol.* 33: 513-522, 1997 |

TABLE 1-continued

Seed Preferred promoters

| GENE SOURCE | EXPRESSION PATTERN | REFERENCE |
|---|---|---|
| rice ADP-glucose PP | endosperm | Trans Res 6: 157-68, 1997 |
| maize ESR gene family | endosperm | Plant J 12: 235-46, 1997 |
| sorgum γ-kafirin | endosperm | PMB 32: 1029-35, 1996 |
| KNOX | embryo | Postma-Haarsma et al, Plant Mol. Biol. 39: 257-71, 1999 |
| rice oleosin | embryo and aleuron | Wu et al, J. Biochem., 123: 386, 1998 |
| sunflower oleosin | seed (embryo and dry seed) | Cummins, et al., Plant Mol. Biol. 19: 873-876, 1992 |
| putative rice 40S ribosomal protein | weak in endosperm | |
| rice alpha-globulin | strong in endosperm | |
| rice alanine aminotransferase | weak in endosperm | |
| trypsin inhibitor ITR1 (barley) | weak in endosperm | |
| rice WSI1S | embryo + stress | |
| rice RAB21 | embryo + stress | |
| rice oleosin 18 kd | aleurone + embryo | |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance or that introduce a new metabolic trait or that allow visual selection. Cells containing the recombinant DNA will thus be able to survive in the presence of antibiotic or herbicide concentrations that kill untransformed cells. Examples of selectable marker genes include the bar gene which provides resistance to the herbicide Basta; the npt gene which confers resistance to the antibiotic kanamycin; the hpt gene which confers hygromycin resistance. Visual markers, such as the Green Fluorescent Protein (GFP, Haseloff et al., 1997), β-glucuronidase (GUS) or luciferase may also be used as selectable markers.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

The cyclin A protein itself and/or the cyclin A nucleic acid itself may be introduced directly into a plant cell or into the plant itself (including introduction into a tissue, organ or any other part of the plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of a plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. A preferred method according to the present invention is the protocol according to Hiei et al. 1994 in the case of rice transformation. For corn transformation, methods comprising Agrobacterium-based transformation of corn tissue have been described previously in EP0604662, EP0672752, EP0971578, EP0955371, EP0558676 etc. Preferred methods to transform corn with a high efficiency are the protocols described in Ishida et al. (High efficiency transformation of maize (*Zea mays* L.) mediated by *Agrobacterium tumefaciens*. Nat Biotechnol. 1996 June; 14(6):745-50) and described in Frame et al. (*Agrobacterium tumefaciens*-mediated transformation of maize embryos using a standard binary vector system. Plant Physiol. 2002 May; 129(1):13-22).

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated cyclin A nucleic acid molecule, preferably encoding a cyclin A protein. Preferred host cells according to the invention are plant cells. The invention also extends to harvestable parts of a plant, such as, but not limited to seeds, leaves, fruits, flowers, stem cultures, stem, rhizomes, roots, tubers and bulbs.

The term "plant" as used herein encompasses whole plants, ancestors and progeny of the plants and plant parts, including seeds, shoots, stems, roots (including tubers), and plant cells, tissues and organs. The term "plant" also therefore encompasses suspension cultures, embryos, meristematic regions, callus tissue, leaves, seeds, roots, shoots, gametophytes, sporophytes, pollen, and microspores.

Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp., *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragana* spp., *Flemingia* spp, *Freycinetia banksii*, *Geranium thunbergii*, *Ginkgo biloba*, *Glycine javanica*, *Gliricidia* spp., *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Omithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trffolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash tea, trees and algae amongst others.

According to a preferred feature of the present invention, the plant is a crop plant comprising tomato, potato, tobacco, rye, soybean, sunflower, canola, alfalfa, rapeseed or cotton. Further preferably, the plant according to the present invention is a monocotyledonous plant such as sugarcane. Most preferably, the plant is a cereal, such as oat, rye, rice, maize, wheat, millet, sorghum or barley.

The present invention also encompasses plants obtainable by the methods according to the present invention. The present invention therefore provides plants obtainable by the method according to the present invention, which plants have increased yield relative to control plants, wherein the plants also have preferential expression of cyclin A in plant seed tissue.

According to another embodiment of the present invention, there is provided a method for the production of transgenic plants having increased yield relative to control plants, comprising introduction into a plant of a cyclin A nucleic acid operably linked to a seed-preferred promoter. The cyclin A may be the nucleic acid according to SEQ ID NO: 1 or may be any one of the variant cyclin A nucleic acids as hereinbefore defined or may be any nucleic acid falling within the definition of a cyclin A nucleic acid as defined hereinabove.

DESCRIPTION OF FIGURES

The present invention will now be described with reference to the following figures in which:

FIG. 3 is a table showing a cross-species conserved motif found in cyclin As. Motif 1 (SEQ ID NOs: 8-19) may be used to distinguish a cyclin A from any other type of cyclin and Motif 1 (SEQ ID NOs: 8-19) and Motif 2 (SEQ ID NOs: 20-31) together can be used to distinguish a A2 cyclin from any other A-type cyclin. By way of control, a motif found in cyclin B;1 is shown.

FIG. 4 is a list of the sequences used in the methods of the invention.

DESCRIPTION OF SEQUENCES

Figure 1:
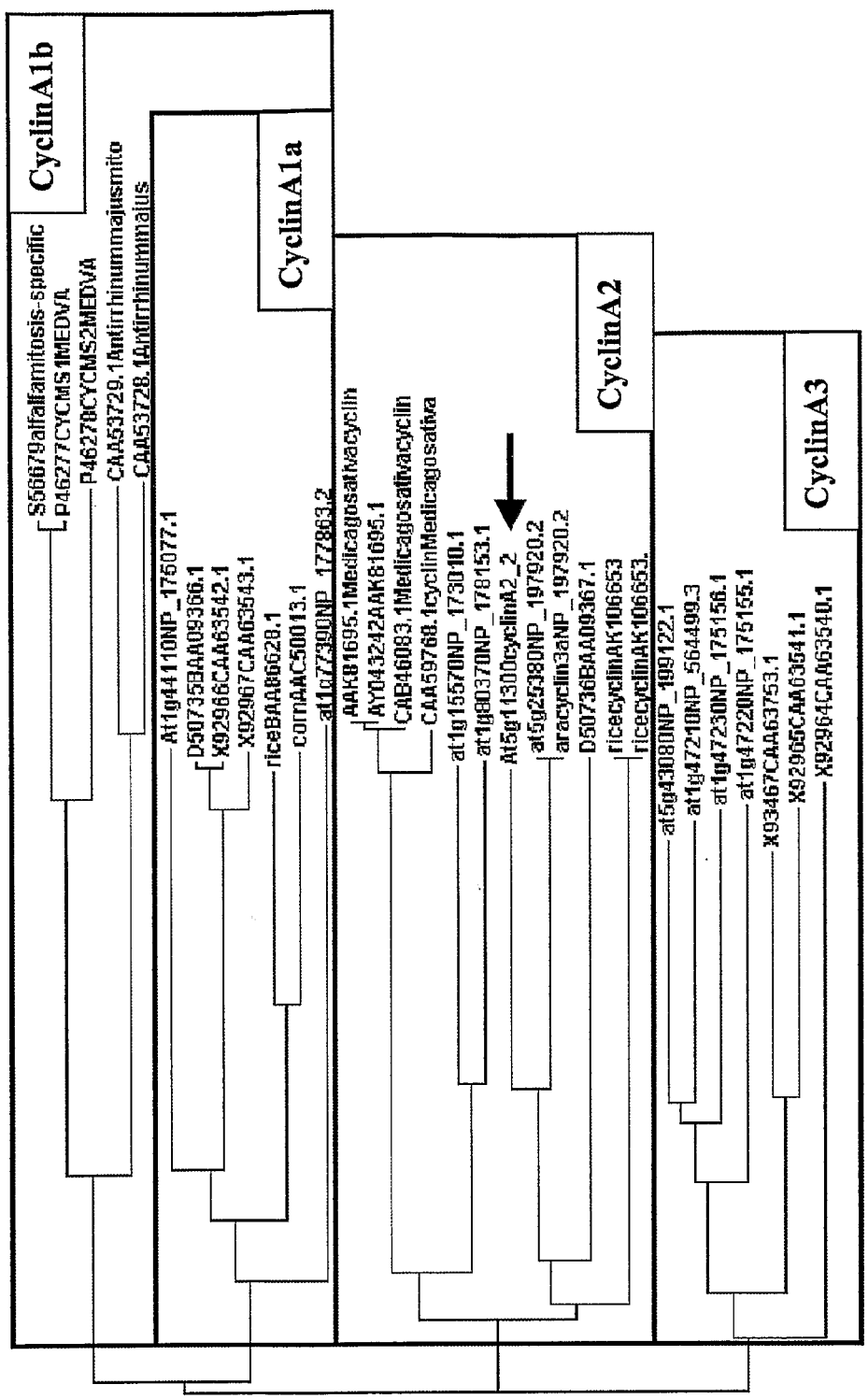
FIG. 1 is a phylogenetic tree prepared by alignment of several full length cyclin A protein sequences (except for 1 partial rice sequence). Alignment was using the Clustal program using default settings and viewed as a phylogram. As shown, the sequences duster in the four major groups shown.

SEQ ID NO: 1 represents the cyclin A2;2 nucleic acid used in the methods according to the invention. It is identical to the coding sequence of the sequence deposited under accession number NM__121168, except for two substitutions, the first at position 851 in which C is substituted for G and the second at position 1295 in which C is substituted for T. These changes are not thought to be of any consequence.

SEQ ID NO: 2 represents the cyclin A2;2 amino acid encoded by the nucleic acid of SEQ ID NO: 1. It is identical to the sequence deposited under accession number NP__568248, except that it contains two amino acid substitutions, the first in which the proline at position 284 is substituted for an arginine and the second in which the serine at position 432 is substituted for a phenylalanine. These changes are not thought to be of any consequence.

SEQ ID NO: 3 is a representation of the prolamin promoter from rice.

SEQ ID NO: 4 and SEQ ID NO: 5 represent the sequences of the primers used for gene cloning.

EXAMPLES

The present invention will now be described with reference to the following examples, which are by way of illustration alone.

DNA Manipulation

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1984), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Gene Cloning

The *Arabidopsis thaliana* cyclin A2;2 (internal reference CDS95) was amplified by PCR using as a template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb, and original number of clones was of 1.59.times.10.sup.7 cfu. Original titer was determined to be 9.6.times.10.sup.5 cfu/ml after first amplification of 6.times.10.sup.11 cfu/ml. After plasmid extraction, 200 ng of template was used in a 50.mu.l PCR mix. Primers prm582 (sense, start codon in bold, AttB1 site in italic: 5' ggggacaagtttgtacaaaaaagca ggcttcacaatgtattgctcttct-tcgatgc 3') (SEQ ID NO:4) and prm583 (reverse, complementary, stop codon in bold, AttB2 site in italic: 5' ggggaccact-tgteacaagaaagctgggtgcttggtgtcatcttgagaatag 3') (SEQ ID NO:5), which include the AttB sites for Gateway recombination, were used for PCR amplification. PCR was performed using Hifi Taq DNA polymerase under standard conditions. A PCR fragment of 1311 bp was amplified and purified also using standard methods. The first step of the Gateway procedure, the BP reaction, was then performed, during which the PCR fragment recombined in vivo with the pDONR201 plasmid to produce, according to the Gateway terminology, an "entry clone", p754. Plasmid pDONR201 was purchased from Invitrogen, as part of the Gateway® technology.

Example 2

Vector Construction

Entry clone p754 containing a cyclin A2.2 was subsequently used in an LR reaction with a destination vector used for *Oryza sativa* transformation. This vector contains as functional elements within the T-DNA borders: a plant selectable marker; a visual marker; and a Gateway cassette intended for LR in vivo recombination with the sequence of interest already cloned in the entry clone. A PROLAMIN promoter for over-expression (PRO90) is located upstream of this Gateway cassette.

Figure 2:
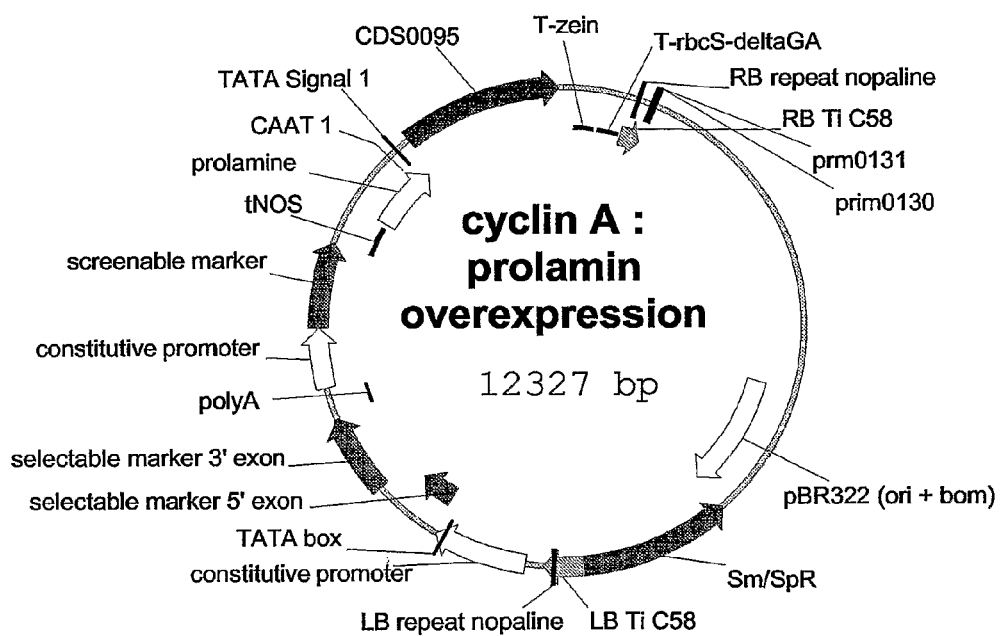
FIG. 2 Binary vector for the expression in *Oryza sativa* of the *Arabidopsis thaliana* cyclin A2;2 gene under the control of the PROLAMIN promoter. This vector contains a T-DNA derived from the Ti Plasmid, limited by a left border (LB repeat, LB Ti C58) and a right border (RB repeat, RB Ti C58)).

After the LR recombination step, the resulting expression vector as shown in FIG. 2 (Cyclin A2;2: prolamin—upregulation) was transformed into Agrobacterium and subsequently into *Oryza sativa* plants. Transformed rice plants were allowed to grow and were then examined for the parameters described in Example 3.

Example 3

Evaluation and Results

A. Statistical Analysis: F-Test

A two factor ANOVA (analysis of variants) was used as statistical model for the overall evaluation of plant phenotypic characteristics. An F-test was carried out on all the parameters measured of all the plants of all the events transformed with the gene of the present invention. The F-test is carried out to check for an effect of the gene over all the transformation events and to verify for an overall effect of the gene, also known as a "global gene effect". If the value of the F-test shows that the data are significant, it is then concluded that there is a "gene" effect, meaning that it more than just the presence or the position of the gene that is causing the differences in phenotype. The threshold for significance for a true global gene effect is set at a 5% probability level for the F-test.

B. Evaluation Protocol

Approximately 15 to 20 independent T0 rice transformants were generated. The primary transformants were transferred from tissue culture chambers to a greenhouse for growing and harvest of T1 seed. Several events, of which the T1 progeny segregated 3:1 for presence/absence of the transgene, were retained. For each of these events, approximately 10 T1 seedlings containing the transgene (hetero- and homo-zygotes), and approximately 10 T1 seedlings lacking the transgene (nullizygotes), were selected.

(i) Vegetative Growth Measurements:

The selected T1 plants (approximately 10 with the transgene and approximately 10 without the transgene) were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity each plant was passed several times through a digital imaging cabinet and imaged. At each time point digital images (2048×1536 pixels, 16 million colours) were taken of each plant from at least 6 different angles. Parameters such as aboveground area were derived in an automated way from the digital images of all the plants using image analysis software.

(ii) Seed-Related Parameter Measurements:

The mature primary panicles were harvested, bagged, barcode-labelled and then dried for three days in the oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. This procedure resulted in the set of seed-related parameters described below.

(a) Total Seed Number

The total seed number was measured by counting the number of husks harvested from a plant. The results for total seed number from plants expressing cyclin A2;2 under the control of a seed-preferred promoter (prolamin) is shown below in Table 2.

TABLE 2

Total seed number cyclin A2;2: seed-preferred promoter (prolamin)
Total Seed Number

| Line | TR | null | dif | % dif | p-value |
|---|---|---|---|---|---|
| Overall | 549.8 | 437.6 | 112.25 | 26 | 0.0397 |

The total seed number for plants expressing a cyclin A2;2 under the control of a constitutive promoter (data not shown) was less than the total number of seeds obtained from plants expressing a cyclin A2;2 gene driven by a prolamin promoter (which as shown above gave a significant p value from the F-test indicating an overall gene effect).

(b) Number of Filled Seeds

The number of filled seeds was determined by counting the number of filled husks that remained after the separation step. The results for the number of filled seeds from plants expressing cyclin A2;2 under the control of a seed-preferred promoter (prolamin) are shown below (Table 3 for T1 plants and Table 4 for T2 plants) verses the results for the number of filled seeds from plants expressing cyclin A2;2 under the control of a constitutive promoter (Table 5).

TABLE 3

T1 Evaluation - Number of filled seeds cyclin A2;2: pProlamin
Number of filled Seeds

| Line | TR | null | dif | % dif | p-value |
|---|---|---|---|---|---|
| Overall | 412.9 | 322.9 | 89.98 | 28 | 0.0261 |

The results show a significant overall gene effect (with a significant p-value from the F-test). T1 transgenic plants show a significant increase in the number of filled seeds relative to control plants.

TABLE 4

T2 Evaluation - Number of filled seeds cyclin A2;2: pProlamin
Number of filled Seeds

| Line | TR | null | dif | % dif | p-value |
|---|---|---|---|---|---|
| Overall | 438.4 | 315.1 | 123.32 | 39 | 0.0139 |

The results show a significant overall gene effect (with a significant p-value from the F-test). T2 transgenic plants show a significant increase in the number of filled seeds relative to control plants.

TABLE 5

Number of filled seeds cyclin A2;2: pGOS2
Number of filled Seeds

| Line | TR | null | dif | % dif | p-value |
|---|---|---|---|---|---|
| Overall | 256.8 | 241.4 | 15.41 | 6 | 0.1007 |

The results show that there is an increase in the number of filled seeds for plants expressing a cyclin A2;2 under the control of a constitutive promoter relative to control plants, however plants expressing cyclin A2;2 under the control of the prolamin promoter show a greater number of filled seeds (see Table 3 and Table 4 above).

(c) Total Seed Yield

The total seed yield per plant was measured by weighing all filled husks harvested from a plant. The results of the total seed yield of plants expressing cyclin A2;2 under the control of pProlamin (see Table 6 for the T1 evaluation results and Table 7 for the results of the T2 evaluation) verses the total seed yield from plants expressing cyclin A2;2 under the control of pGOS2 (see Table 8) are shown below.

TABLE 6

T1 Evaluation - Total seed yield cyclin A2;2: pProlamin
Number of filled Seeds

| Line | TR | null | dif | % dif | p-value |
|---|---|---|---|---|---|
| Overall | 9 | 6.9 | 2.07 | 30 | 0.0211 |

The results of the T1 evaluation show an overall gene effect with a significant p-value from the F-test.

TABLE 7

T2 Evaluation - Total seed yield cyclin A2;2: pProlamin
Number of filled Seeds

| Line | TR | null | dif | % dif | p-value |
|---|---|---|---|---|---|
| Overall | 9.5 | 6.6 | 2.85 | 43 | 0.0128 |

The results of the T2 evaluation show an overall gene effect with a significant p-value from the F-test.

TABLE 8

Total seed yield cyclin A2;2: pGOS2
Total Seed Weight

| Line | TR | null | dif | % dif | p-value |
|---|---|---|---|---|---|
| Overall | 6.3 | 5.7 | 0.6 | 11 | 0.0803 |

As shown in Table 8, the total seed yield for plants expressing cyclin A2;2 constitutively are not as good as the results for seed-preferred expression (see Table 6 and Table 7 above).

(d) Harvest Index

The harvest index is defined herein as the ratio between the total seed yield and the above ground area ($mm^2$), multiplied by a factor $10^6$. The harvest index for plants expressing cyclin A2;2 under the control of a seed-preferred promoter (prolamin) is shown below in Table 9.

TABLE 9

Harvest index cyclin A2;2: pProlamin
Harvest Index

| Line | TR | null | dif | % dif | p-value |
|---|---|---|---|---|---|
| Overall | 103.7 | 83.4 | 20.29 | 24 | 0.0711 |

The harvest index for cyclin A2;2: pProlamin-expressing plants shows that there is an overall gene effect (see the p-value from the F-test). The harvest index for plants expressing cyclin A2;2 under the control of a constitutive promoter (results not shown) was not as good as the results shown in Table 9 above.

(e) Thousand Kernel Weight (TKW)

TKW is extrapolated from the number of filled seeds counted and their total weight. The results for TKW of plants expressing cyclin A2;2: pProlamin (see Table 10) verses the TKW of plants expressing cyclin A2;2: pGOS2 (see Table 11) are shown below.

TABLE 10

TKW cyclin A2;2: pProlamin
TKW

| Line | TR | null | dif | % dif | p-value |
|---|---|---|---|---|---|
| Overall | 21.1 | 19.9 | 1.26 | 6 | 0.108 |

An overall gene effect is evident from the table above which shows a significant p-value from the F-test.

TABLE 11

TKW cyclin A2;2: pGOS2
TKW

| Line | TR | null | dif | % dif | p-value |
|---|---|---|---|---|---|
| Overall | 24 | 23.3 | 0.7 | 3 | 0.1509 |

The results for TKW for cyclin A2;2: pGOS2 show an increase in TKW, but the increase is not as great as the increase shown in Table 10 above.

(iii) Stress Evaluation: cyclin A2;2: pProlamin

Seeds were sown and, ten days later, seedlings were transplanted into 10 cm diameter pots filled with a 1:1 mixture of moist sand and vermiculite. The 10 cm diameter pots were inserted into 12 cm diameter pots with one layer of plastic cloth between the two pots to prevent the substrate from leaching out. The pots were then soaked with fresh water before transplantation. One day after transplantation, seedlings were submitted to the salt conditions. The pots were watered 4 times per day at 8 am, 12 am, 4 pm, and 9 pm with a salt-stress inducing nutrient solution containing the following elements:

NPK Nutrient mix, 20-20-20 Peters professional (Scotts) at the concentration of 1 $kg/m^3$ Magnesium chelate, Chelal Mg (BMS, Bornem, Belgium) at 333.33 $ml/m^3$ Iron chelate, Libfer (CIBA, Bradford, UK) at 21.67 $g/m^3$ NaCl 1.425 kg/m3

The salt concentration was monitored on a weekly basis with additions where necessary. Plants were grown under salt-stress conditions until the start of grain filling. At this point, they were transferred to a different compartment of the greenhouse where they were irrigated daily with fresh water until seed harvest. The following parameters were then measured and recorded in the same way as for the non-stressed plants as indicated in (a) to (e) above.

TABLE 12

Total seed yield cyclin A2;2: pProlamin
Total Seed Weight

| Line | TR | null | dif | % dif | p-value |
|---|---|---|---|---|---|
| Overall | 1.3 | 0.9 | 0.47 | 55 | 0.0217 |

The results shown in Table 12 show a significant gene effect as evident from the p-value of the F-test for cyclin A2;2: pProlamin plants under stressed conditions as exemplified by salt stress.

TABLE 13

Number of filled seeds cyclin A2;2: pProlamin
Number of Filled Seeds

| Line | TR | null | dif | % dif | p-value |
|---|---|---|---|---|---|
| Overall | 70.8 | 48.5 | 22.33 | 46 | 0.0396 |

The results shown in Table 13 show a significant gene effect as evident from the p-value of the F-test for cyclin A2;2: pProlamin plants under stressed conditions as exemplified by salt stress.

TABLE 14

Total number of seeds cyclin A2;2: pProlamin
Total Seed Number

| Line | TR | null | dif | % dif | p-value |
|---|---|---|---|---|---|
| Overall | 140.7 | 105.1 | 35.55 | 34 | 0.0594 |

The results shown in Table 14 show an increase in the total number of seeds relative to control plants.

TABLE 15

Harvest Index cyclin A2;2: pProlamin
Harvest Index

| Line | TR | null | dif | % dif | p-value |
|---|---|---|---|---|---|
| Overall | 62.1 | 30.4 | 31.64 | 104 | 0.3522 |

The results shown in Table 15 show an increase in the harvest index relative to control plants.

TABLE 16

TKW cyclin A2;2: pProlamin
TKW

| Line | TR | null | dif | % dif | p-value |
|---|---|---|---|---|---|
| Overall | 18.4 | 17.4 | 0.98 | 6 | 0.0269 |

The results shown in Table 16 show a significant gene effect as evident from the p-value of the F-test for cyclin A2;2: pProlamin plants under stressed conditions as exemplified by salt stress.

Example 4

Application of the Invention in Maize

The invention described herein can also be used in maize. A cyclin A is cloned under control of a seed-preferred promoter in a plant transformation vector suited for *Agrobacterium*-mediated corn transformation. Such vectors and methods for corn transformation have been described in literature (EP0604662, EP0672752, EP0971578, EP0955371, EP0558676, Ishida et al. 1996; Frame et al., 2002).

Transgenic plants made by these methods are grown in the greenhouse for T1 seed production. Inheritability and copy number of the transgene is checked by quantitative real-time PCR and Southern blot analysis and expression levels of the transgene is determined by reverse PCR and Northern analysis. Transgenic lines with single copy insertions of the transgene and with varying levels of transgene expression are selected for T2 seed production. Progeny seeds are germinated and grown in the greenhouse in conditions adapted for maize (16:8 photoperiod, 26-28° C. daytime temperature and 22-24° C. nighttime temperature) as well under water-deficient, nitrogen-deficient, and excess NaCl conditions.

In the case of selfing, null segregants from the same parental line, as well as wild type plants of the same cultivar are used as controls. The progeny plants resulting from the selfing or crosses are evaluated for different biomass and growth parameters, including plant height, stalk/stem thickness, number of leaves, total above ground area, leaf greenness, time to maturity, time to silking, flowering time, ear number, ear length, row number, kernel number, kernel size, kernel oil content, grain maturity, harvest time. Lines that are most significantly improved for any of the above-mentioned parameters are selected for further field testing and marker-assisted breeding, with the objective of transferring the field-validated transgenic traits into commercial germplasm. Methods for testing maize for growth and yield-related parameters in the field are well established in the art, as are techniques for introgressing specific loci (such as transgene containing loci) from one germplasm into another. This also includes transferring a trait(s) of interest from a transformed inbred line to a commercial hybrid with desirable added agronomic or nutritional or medical value.

The invention claimed is:

1. A method for increasing plant yield, said method comprising: (a) introducing into a plant a cyclin A nucleic acid molecule encoding a cyclin A protein, said cyclin A protein comprising a motif consisting of W L V/I E V S/A D/E D/E Y K/R/T L (SEQ ID NO:6), wherein said cyclin A nucleic acid molecule is operably linked to a seed-preferred promoter; and (b) selecting a plant exhibiting at least one of increased seed weight, increased number of filled seeds, increased seed number, increased seed size, increased harvest index, increased thousand kernel weight or modified seed composition, each relative to a corresponding control plant.

2. The method according to claim 1 wherein said cyclin A nucleic acid molecule is a cyclin A2 nucleic acid molecule encoding a cyclin A2 protein selected from cyclin A2;1, cyclin A2;2, cyclin A2;3 and cyclin A2;4, said cyclin A2 protein comprising a motif consisting of: E L T L V/I/T/M D/E/M Y T/S/H/P/G F R/L U R/K/N F L P S (SEQ ID NO:7), having at least two of residues (- -T- - - - -F- -F- - -).

3. The method according to claim 1 wherein said seed-preferred promoter is a promoter active in the endosperm.

4. The method according to claim 3, wherein said promoter is a prolamin promoter.

5. The method according claim 2, wherein said increased yield is achieved in optimal and sub-optimal growing conditions.

6. The method according to claim 5, wherein said sub-optimal growing condition comprises abiotic stress.

7. The method according to claim 1 wherein said plant is selected from rice, maize, wheat, barley, soybean, sunflower, canola, sugarcane, alfalfa, millet, barley, rapeseed, sorghum and cotton.

8. Plants obtainable by a method according to claim 2.

9. The method according to claim 6, wherein said abiotic stress is salt stress.

* * * * *

SEQUENCE LISTING

```
<160> NUMBER OF SEQ ID NOS: 31

<210> SEQ ID NO 1
<211> LENGTH: 1311
<212> TYPE: DNA
<213> ORGANISM: Arabidopsis thaliana
<220> FEATURE:
<221> NAME/KEY: misc_feature
<223> OTHER INFORMATION: A variant of the coding sequence of the
      sequence deposited under accession number NM_121168 contains a G
      instead of C on position 851 and a T instead of C on position 1295

<400> SEQUENCE: 1
atgtattgct cttcttcgat gcatccaaat gcaaacaaag aaaatatctc tacttcagat      60
gtacaggaga gttttgtacg aataacgaga tcacgagcta aaaaagccat gggaagagga     120
gtatcaatac ctccaacaaa accttctttt aaacagcaaa agagacgtgc agtacttaag     180
gatgtgagta ataccctctgc agatattatt tattcagaac ttcgaaaggg aggcaacatc     240
aaggcaaaca gaaaatgtct aaaagagcct aaaaaagcag caaggaagg tgctaacagt     300 gccatggata ttctggtaga tatgcataca gaaaaatcaa aattagcaga agatttgtcc     360
```

-continued

```
aagatcagga tggctgaagc ccaagatgtc tctctttcaa actttaaaga tgaagaaatt    420
actgagcaac aagaagatgg atcaggtgtc atggagttac ttcaagttgt agatattgat    480
tccaacgtcg aagatccaca gtgttgcagc ttgtatgctg ctgatatata tgacaacata    540
catgttgcag agcttcaaca acgacccttg gctaattata tggagcttgt gcagcgagat    600
atcgacccag acatgagaaa gattctgatt gactggcttg tagaagtttc tgacgactac    660
aagctggttc cagatacgct ttaccttaca gtgaatctta tcgaccggtt tctgtccaac    720
agttacattg aaaggcaaag actccagctc cttggtgtct cttgcatgct tatagcttca    780
aaatatgaag agctttccgc accaggggtg gaggagtttt gcttcattac ggccaacaca    840
tacacaagac cagaagtgct gagcatggag attcaaattc taaattttgt gcactttaga    900
ttatcggttc ctaccaccaa acatttctg aggcggttca ttaaagcagc tcaagcttcg    960
tacaaggtgc ctttcattga actggagtat ttagcaaact atctcgccga attgacactg   1020
gtggaatata gttcctaag gttcctgcca tcactaattg ctgcttcagc tgttttccta   1080
gcccgatgga cactcgacca aactgaccat ccttggaacc ctactctgca acactacacc   1140
agatatgagg tagctgagct gaagaacaca gttctcgcca tggaggactt gcagctcaac   1200
accagtggct gtactctcgc tgccacccgt gagaaataca accaaccaaa gtttaagagc   1260
gtggcaaagc tgacatctcc caaacgagtc acatcactat tctcaagatg a            1311
```

<210> SEQ ID NO 2
<211> LENGTH: 436
<212> TYPE: PRT
<213> ORGANISM: Arabidopsis thaliana
<220> FEATURE:
<221> NAME/KEY: MISC_FEATURE
<223> OTHER INFORMATION: A variant of the sequence deposited under
      accession number NP_568248 contains an arginine instead of a
      proline on position 284 and a phenylalanine instead of a serine on
      position 432

<400> SEQUENCE: 2

```
Met Tyr Cys Ser Ser Met His Pro Asn Ala Asn Lys Glu Asn Ile
1               5                   10                  15

Ser Thr Ser Asp Val Gln Glu Ser Phe Val Arg Ile Thr Arg Ser Arg
            20                  25                  30

Ala Lys Lys Ala Met Gly Arg Gly Val Ser Ile Pro Pro Thr Lys Pro
        35                  40                  45

Ser Phe Lys Gln Gln Lys Arg Arg Ala Val Leu Lys Asp Val Ser Asn
    50                  55                  60

Thr Ser Ala Asp Ile Ile Tyr Ser Glu Leu Arg Lys Gly Gly Asn Ile
65                  70                  75                  80

Lys Ala Asn Arg Lys Cys Leu Lys Glu Pro Lys Ala Ala Lys Glu
                85                  90                  95

Gly Ala Asn Ser Ala Met Asp Ile Leu Val Asp Met His Thr Glu Lys
            100                 105                 110

Ser Lys Leu Ala Glu Asp Leu Ser Lys Ile Arg Met Ala Glu Ala Gln
        115                 120                 125

Asp Val Ser Leu Ser Asn Phe Lys Asp Glu Glu Ile Thr Glu Gln Gln
    130                 135                 140

Glu Asp Gly Ser Gly Val Met Glu Leu Leu Gln Val Val Asp Ile Asp
145                 150                 155                 160

Ser Asn Val Glu Asp Pro Gln Cys Cys Ser Leu Tyr Ala Ala Asp Ile
                165                 170                 175

Tyr Asp Asn Ile His Val Ala Glu Leu Gln Gln Arg Pro Leu Ala Asn
```

```
                        180                 185                 190
Tyr Met Glu Leu Val Gln Arg Asp Ile Asp Pro Asp Met Arg Lys Ile
            195                 200                 205

Leu Ile Asp Trp Leu Val Glu Val Ser Asp Asp Tyr Lys Leu Val Pro
        210                 215                 220

Asp Thr Leu Tyr Leu Thr Val Asn Leu Ile Asp Arg Phe Leu Ser Asn
225                 230                 235                 240

Ser Tyr Ile Glu Arg Gln Arg Leu Gln Leu Leu Gly Val Ser Cys Met
                245                 250                 255

Leu Ile Ala Ser Lys Tyr Glu Glu Leu Ser Ala Pro Gly Val Glu Glu
            260                 265                 270

Phe Cys Phe Ile Thr Ala Asn Thr Tyr Thr Arg Pro Glu Val Leu Ser
        275                 280                 285

Met Glu Ile Gln Ile Leu Asn Phe Val His Phe Arg Leu Ser Val Pro
    290                 295                 300

Thr Thr Lys Thr Phe Leu Arg Arg Phe Ile Lys Ala Ala Gln Ala Ser
305                 310                 315                 320

Tyr Lys Val Pro Phe Ile Glu Leu Glu Tyr Leu Ala Asn Tyr Leu Ala
                325                 330                 335

Glu Leu Thr Leu Val Glu Tyr Ser Phe Leu Arg Phe Leu Pro Ser Leu
            340                 345                 350

Ile Ala Ala Ser Ala Val Phe Leu Ala Arg Trp Thr Leu Asp Gln Thr
        355                 360                 365

Asp His Pro Trp Asn Pro Thr Leu Gln His Tyr Thr Arg Tyr Glu Val
    370                 375                 380

Ala Glu Leu Lys Asn Thr Val Leu Ala Met Glu Asp Leu Gln Leu Asn
385                 390                 395                 400

Thr Ser Gly Cys Thr Leu Ala Ala Thr Arg Glu Lys Tyr Asn Gln Pro
                405                 410                 415

Lys Phe Lys Ser Val Ala Lys Leu Thr Ser Pro Lys Arg Val Thr Ser
            420                 425                 430

Leu Phe Ser Arg
        435

<210> SEQ ID NO 3
<211> LENGTH: 654
<212> TYPE: DNA
<213> ORGANISM: Oryza sativa

<400> SEQUENCE: 3
cttctacatc ggcttaggtg tagcaacacg actttattat tattattatt attattatta       60
ttattttaca aaaatataaa atagatcagt ccctcaccac aagtagagca agttggtgag      120
ttattgtaaa gttctacaaa gctaatttaa aagttattgc attaacttat ttcatattac      180
aaacaagagt gtcaatggaa caatgaaaac catatgacat actataattt tgtttttatt      240
attgaaatta taaattcaa agagaataaa tccacatagc cgtaaagttc tacatgtggt       300
gcattaccaa aatatatata gcttacaaaa catgacaagc ttagtttgaa aaattgcaat      360
ccttatcaca ttgacacata aagtgagtga tgagtcataa tattattttc tttgctaccc      420
atcatgtata tatgatagcc acaaagttac tttgatgatg atatcaaaga acatttttag      480
gtgcacctaa cagaatatcc aaataatatg actcacttag atcataatag agcatcaagt      540
aaaactaaca ctctaaagca accgatggga aagcatctat aaatagacaa gcacaatgaa      600
aatcctcatc atccttcacc acaattcaaa tattatagtt gaagcatagt agta            654
```

-continued

<210> SEQ ID NO 4
<211> LENGTH: 56
<212> TYPE: DNA
<213> ORGANISM: Artificial sequence
<220> FEATURE:
<223> OTHER INFORMATION: primer PRM582

<400> SEQUENCE: 4
ggggacaagt ttgtacaaaa aagcaggctt cacaatgtat tgctcttctt cgatgc    56

<210> SEQ ID NO 5
<211> LENGTH: 52
<212> TYPE: DNA
<213> ORGANISM: Artificial sequence
<220> FEATURE:
<223> OTHER INFORMATION: primer PRM583

<400> SEQUENCE: 5
ggggaccact ttgtacaaga aagctgggtg cttggtgtca tcttgagaat ag        52

<210> SEQ ID NO 6
<211> LENGTH: 11
<212> TYPE: PRT
<213> ORGANISM: Unknown
<220> FEATURE:
<223> OTHER INFORMATION: motif 1, found in cyclin A proteins
<220> FEATURE:
<221> NAME/KEY: misc_feature
<222> LOCATION: 3
<223> OTHER INFORMATION: Xaa at position 3 may be Val or Ile
<220> FEATURE:
<221> NAME/KEY: misc_feature
<222> LOCATION: 6
<223> OTHER INFORMATION: Xaa at position 6 may be Ser or Ala
<220> FEATURE:
<221> NAME/KEY: misc_feature
<222> LOCATION: 7
<223> OTHER INFORMATION: Xaa at position 7 may be Asp or Glu
<220> FEATURE:
<221> NAME/KEY: misc_feature
<222> LOCATION: 8
<223> OTHER INFORMATION: Xaa at position 8 may be Asp or Glu
<220> FEATURE:
<221> NAME/KEY: misc_feature
<222> LOCATION: 10
<223> OTHER INFORMATION: Xaa at positon 10 may be Lys, Arg or Thr

<400> SEQUENCE: 6

Trp Leu Xaa Glu Val Xaa Xaa Xaa Tyr Xaa Leu
1               5                   10

<210> SEQ ID NO 7
<211> LENGTH: 15
<212> TYPE: PRT
<213> ORGANISM: Unknown
<220> FEATURE:
<223> OTHER INFORMATION: motif 2, found in cyclin A2 proteins
<220> FEATURE:
<221> NAME/KEY: misc_feature
<222> LOCATION: 5
<223> OTHER INFORMATION: Xaa at position 5 may be Val, Ile, Thr or Met
<220> FEATURE:
<221> NAME/KEY: misc_feature
<222> LOCATION: 6
<223> OTHER INFORMATION: Xaa at position 6 may be Asp, Glu or Met
<220> FEATURE:
<221> NAME/KEY: misc_feature
<222> LOCATION: 8
<223> OTHER INFORMATION: Xaa at position 8 may be Thr, Ser, His, Pro or
      Gly
<220> FEATURE:
<221> NAME/KEY: misc_feature
<222> LOCATION: 10

```
<223> OTHER INFORMATION: Xaa at position 10 may be Arg or Leu
<220> FEATURE:
<221> NAME/KEY: misc_feature
<222> LOCATION: 11
<223> OTHER INFORMATION: Xaa at position 11 may be Leu, Arg, Lys or Asn

<400> SEQUENCE: 7

Glu Leu Thr Leu Xaa Xaa Tyr Xaa Phe Xaa Xaa Phe Leu Pro Ser
1               5                   10                  15

<210> SEQ ID NO 8
<211> LENGTH: 15
<212> TYPE: PRT
<213> ORGANISM: Arabidopsis thaliana

<400> SEQUENCE: 8

Trp Leu Val Glu Val Ser Glu Glu Tyr Lys Leu Val Ser Asp Thr
1               5                   10                  15

<210> SEQ ID NO 9
<211> LENGTH: 15
<212> TYPE: PRT
<213> ORGANISM: Arabidopsis thaliana

<400> SEQUENCE: 9

Trp Leu Val Glu Val Ser Asp Asp Tyr Lys Leu Val Pro Asp Thr
1               5                   10                  15

<210> SEQ ID NO 10
<211> LENGTH: 15
<212> TYPE: PRT
<213> ORGANISM: Arabidopsis thaliana

<400> SEQUENCE: 10

Trp Leu Val Glu Val Ser Glu Glu Tyr Thr Leu Ala Ser Asp Thr
1               5                   10                  15

<210> SEQ ID NO 11
<211> LENGTH: 15
<212> TYPE: PRT
<213> ORGANISM: Arabidopsis thaliana

<400> SEQUENCE: 11

Trp Leu Val Glu Val Ser Glu Glu Tyr Thr Leu Val Pro Asp Thr
1               5                   10                  15

<210> SEQ ID NO 12
<211> LENGTH: 15
<212> TYPE: PRT
<213> ORGANISM: Oryza sativa

<400> SEQUENCE: 12

Trp Leu Val Glu Val Ser Glu Glu Tyr Lys Leu Val Pro Asp Thr
1               5                   10                  15

<210> SEQ ID NO 13
<211> LENGTH: 15
<212> TYPE: PRT
<213> ORGANISM: Medicago

<400> SEQUENCE: 13

Trp Leu Val Glu Val Ser Glu Gly Tyr Lys Leu Gln Ala Asn Thr
1               5                   10                  15

<210> SEQ ID NO 14
<211> LENGTH: 15
```

```
<212> TYPE: PRT
<213> ORGANISM: Nicotiana tabacum

<400> SEQUENCE: 14

Trp Leu Val Glu Val Ser Glu Glu Tyr Arg Leu Val Pro Asp Thr
1               5                   10                  15

<210> SEQ ID NO 15
<211> LENGTH: 15
<212> TYPE: PRT
<213> ORGANISM: Arabidopsis thaliana

<400> SEQUENCE: 15

Trp Leu Ile Glu Val Ser Glu Glu Tyr Arg Leu Val Pro Glu Thr
1               5                   10                  15

<210> SEQ ID NO 16
<211> LENGTH: 15
<212> TYPE: PRT
<213> ORGANISM: Arabidopsis thaliana

<400> SEQUENCE: 16

Trp Leu Val Glu Val Ala Glu Glu Tyr Arg Leu Ser Pro Glu Thr
1               5                   10                  15

<210> SEQ ID NO 17
<211> LENGTH: 15
<212> TYPE: PRT
<213> ORGANISM: Arabidopsis thaliana

<400> SEQUENCE: 17

Trp Leu Val Glu Val Ala Glu Glu Tyr Lys Leu Leu Ser Asp Thr
1               5                   10                  15

<210> SEQ ID NO 18
<211> LENGTH: 15
<212> TYPE: PRT
<213> ORGANISM: Oryza sativa

<400> SEQUENCE: 18

Trp Leu Val Glu Val Ala Glu Glu Tyr Arg Leu Val Pro Asp Thr
1               5                   10                  15

<210> SEQ ID NO 19
<211> LENGTH: 15
<212> TYPE: PRT
<213> ORGANISM: Arabidopsis thaliana

<400> SEQUENCE: 19

Trp Leu Ile Asp Val His Val Arg Phe Glu Leu Asn Pro Glu Thr
1               5                   10                  15

<210> SEQ ID NO 20
<211> LENGTH: 15
<212> TYPE: PRT
<213> ORGANISM: Arabidopsis thaliana

<400> SEQUENCE: 20

Glu Leu Thr Leu Thr Glu Tyr Thr Phe Arg Leu Phe Leu Pro Ser
1               5                   10                  15

<210> SEQ ID NO 21
<211> LENGTH: 15
<212> TYPE: PRT
<213> ORGANISM: Arabidopsis thaliana
```

-continued

```
<400> SEQUENCE: 21

Glu Leu Thr Leu Val Glu Tyr Ser Phe Leu Arg Phe Leu Pro Ser
1               5                   10                  15

<210> SEQ ID NO 22
<211> LENGTH: 15
<212> TYPE: PRT
<213> ORGANISM: Arabidopsis thaliana

<400> SEQUENCE: 22

Glu Leu Thr Leu Ile Asp Tyr His Phe Leu Lys Phe Leu Pro Ser
1               5                   10                  15

<210> SEQ ID NO 23
<211> LENGTH: 15
<212> TYPE: PRT
<213> ORGANISM: Arabidopsis thaliana

<400> SEQUENCE: 23

Glu Leu Thr Leu Met Asp Tyr Pro Phe Leu Lys Phe Leu Pro Ser
1               5                   10                  15

<210> SEQ ID NO 24
<211> LENGTH: 15
<212> TYPE: PRT
<213> ORGANISM: Oryza sativa

<400> SEQUENCE: 24

Glu Leu Thr Leu Ile Asp Tyr Ser Phe Leu Lys Phe Leu Pro Ser
1               5                   10                  15

<210> SEQ ID NO 25
<211> LENGTH: 15
<212> TYPE: PRT
<213> ORGANISM: Medicago

<400> SEQUENCE: 25

Glu Leu Thr Leu Met Asn Tyr Gly Phe Leu Asn Phe Leu Pro Ser
1               5                   10                  15

<210> SEQ ID NO 26
<211> LENGTH: 15
<212> TYPE: PRT
<213> ORGANISM: Nicotiana tabacum

<400> SEQUENCE: 26

Glu Leu Thr Leu Val Asp Tyr Gly Phe Leu Lys Phe Leu Pro Ser
1               5                   10                  15

<210> SEQ ID NO 27
<211> LENGTH: 15
<212> TYPE: PRT
<213> ORGANISM: Arabidopsis thaliana

<400> SEQUENCE: 27

Glu Leu Ser Leu Leu Glu Tyr Thr Met Leu Ser His Ser Pro Ser
1               5                   10                  15

<210> SEQ ID NO 28
<211> LENGTH: 15
<212> TYPE: PRT
<213> ORGANISM: Arabidopsis thaliana

<400> SEQUENCE: 28

Glu Leu Ser Leu Leu Asp Tyr Ala Met Leu Arg Tyr Ala Pro Ser
```

```
<210> SEQ ID NO 29
<211> LENGTH: 15
<212> TYPE: PRT
<213> ORGANISM: Arabidopsis thaliana

<400> SEQUENCE: 29

Glu Leu Ser Met Leu Asp Tyr Gln Ser Val Lys Phe Leu Pro Ser
1               5                   10                  15

<210> SEQ ID NO 30
<211> LENGTH: 15
<212> TYPE: PRT
<213> ORGANISM: Oryza sativa

<400> SEQUENCE: 30

Glu Leu Ser Leu Leu Glu Tyr Asn Leu Leu Ser Tyr Pro Pro Ser
1               5                   10                  15

<210> SEQ ID NO 31
<211> LENGTH: 16
<212> TYPE: PRT
<213> ORGANISM: Arabidopsis thaliana

<400> SEQUENCE: 31

Glu Leu Gly Val Met His Tyr Asp Thr Met Ile Met Phe Ser Pro Ser
1               5                   10                  15
```